(12) United States Patent
Dobson et al.

(10) Patent No.: US 11,944,790 B2
(45) Date of Patent: Apr. 2, 2024

(54) INJECTION DEVICE

(71) Applicant: Owen Mumford Limited, Woodstock (GB)

(72) Inventors: Matthew John Dobson, Woodstock (GB); Rosie Hutt, Woodstock (GB); Abiodun Falodi, Woodstock (GB)

(73) Assignee: Owen Mumford Limited, Oxfordshire (GB)

( * ) Notice: Subject to any disclaimer, the term of this patent is extended or adjusted under 35 U.S.C. 154(b) by 594 days.

(21) Appl. No.: 17/276,006

(22) PCT Filed: Sep. 13, 2019

(86) PCT No.: PCT/EP2019/074521
§ 371 (c)(1),
(2) Date: Mar. 12, 2021

(87) PCT Pub. No.: WO2020/053404
PCT Pub. Date: Mar. 19, 2020

(65) Prior Publication Data
US 2022/0040408 A1   Feb. 10, 2022

(30) Foreign Application Priority Data
Sep. 13, 2018   (GB) ..................... 1814914

(51) Int. Cl.
*A61M 5/20* (2006.01)
*A61M 5/315* (2006.01)
*A61M 5/32* (2006.01)

(52) U.S. Cl.
CPC ...... *A61M 5/2033* (2013.01); *A61M 5/31501* (2013.01); *A61M 5/3204* (2013.01);
(Continued)

(58) Field of Classification Search
CPC ............ A61M 5/2033; A61M 5/31501; A61M 5/3204; A61M 2005/2026;
(Continued)

(56) References Cited

U.S. PATENT DOCUMENTS

| 9,849,242 | B2 | 12/2017 | Henley et al. |
| 2013/0296795 | A1 | 11/2013 | Ekman et al. |
| 2017/0095613 | A1 | 4/2017 | Moller |
| 2017/0232201 | A1 | 8/2017 | Holland et al. |
| 2019/0298924 | A1* | 10/2019 | Gibson ................... A61M 5/20 |

(Continued)

FOREIGN PATENT DOCUMENTS

| EP | 2583706 A1 | 4/2013 |
| TW | 201700117 A | 1/2017 |
| WO | 2018167498 A1 | 9/2018 |

OTHER PUBLICATIONS

International Preliminary Report on Patentability (IPRP) from corresponding PCT Application No. PCT/EP2019/074521, dated Mar. 9, 2021 (12 pages).

(Continued)

*Primary Examiner* — Dung T Ulsh
(74) *Attorney, Agent, or Firm* — Quarles & Brady LLP

(57) ABSTRACT

Injection device including a casing, a syringe carrier located within a proximal end of the casing and being movable along a longitudinal axis of the device between a stowed position and a needle insertion position, a drive assembly located within a distal end of the casing and being movable by an insertion driver in order to move the syringe carrier and a loaded syringe from a stowed position to a needle insertion position; a first formation fixed relative to the casing and a second formation fixed relative to an insertion tube of the drive assembly, the first and second formations defining a plurality of stop positions for the insertion tube relative to the casing, spaced along the direction of said longitudinal axis, to prevent significant rearward movement of the inser- (Continued)

tion tube along said axis when a plunger of a firing cartridge is released from a reaction assembly of the cartridge.

20 Claims, 9 Drawing Sheets

(52) U.S. Cl.
CPC ............... *A61M 2005/2026* (2013.01); *A61M 2005/206* (2013.01); *A61M 2005/2073* (2013.01); *A61M 2005/208* (2013.01); *A61M 2205/581* (2013.01)

(58) Field of Classification Search
CPC .... A61M 2005/206; A61M 2005/2073; A61M 2005/208; A61M 2205/581
See application file for complete search history.

(56) References Cited

U.S. PATENT DOCUMENTS

2021/0030963 A1* 2/2021 Dasbach ................ A61M 5/50
2021/0178082 A1* 6/2021 Franke ............. A61M 5/31501

OTHER PUBLICATIONS

International Search Report and Written Opinion of the International Searching Authority from corresponding PCT Application No. PCT/EP2019/074521, dated Apr. 3, 2020 (18 pages).
Combined Search and Exam Report, related UK Application No. GB1814914.6, dated Feb. 20, 2019 (6 pages).
Taiwan Intellectual Property Office, Search and Examination Report for corresponding TW Application No. 108133253, dated Dec. 9, 2022 (8 pages).

* cited by examiner

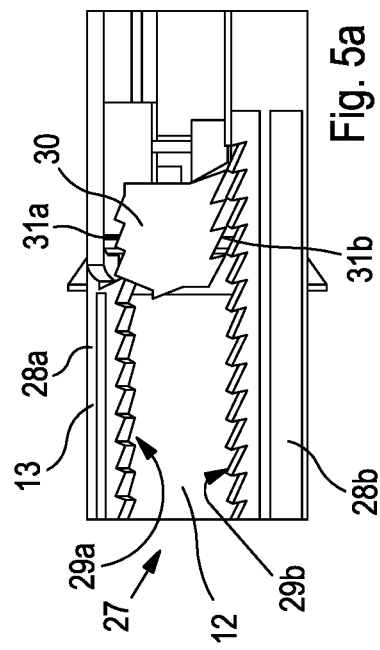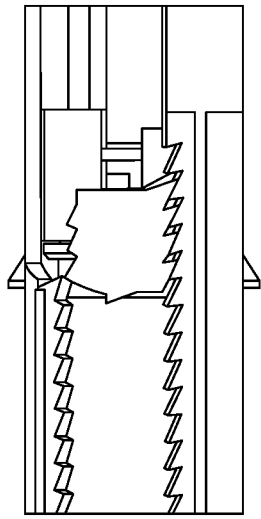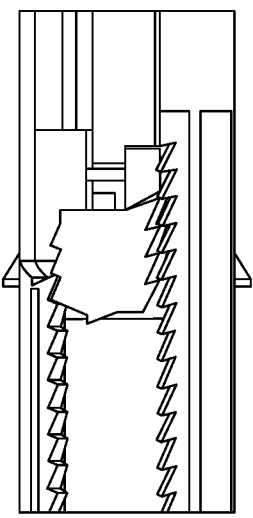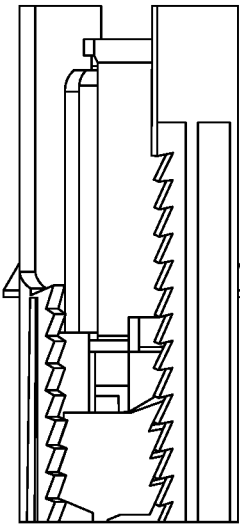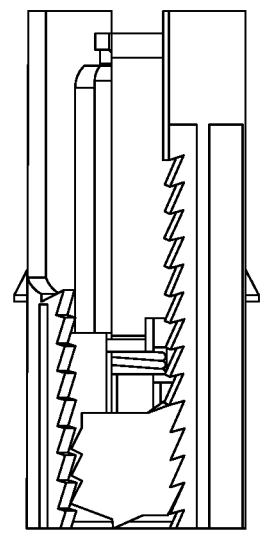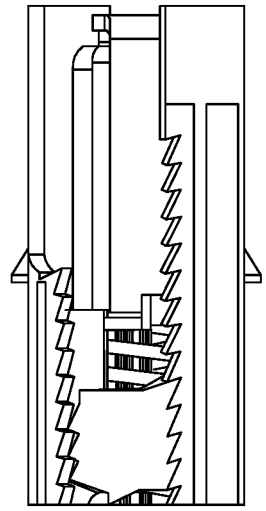

INJECTION DEVICE

CROSS-REFERENCE TO RELATED APPLICATIONS

The present application represents the United States National Stage of International Application No. PCT/EP2019/074521, filed Sep. 13, 2019, which relates to and claims priority to British Patent Application Serial No. GB 1814914.6, filed Sep. 13, 2018, both of which are incorporated herein by reference in their entirety.

TECHNICAL FIELD

This invention relates to an injection device which facilitates powered or power assisted needle insertion and drug delivery.

BACKGROUND

Injection devices are used for the convenient administration of medicaments. For example, injection devices (which may typically be in the form of a pen injector) may be used for providing a single metered dose of a medicament, for example such as Epinephrine in an emergency or for providing regular metered doses of a medicament such as Insulin. Such devices may be either single use "disposable" devices in which the device is typically provided with a syringe already installed, and which is not user-replaceable, or "reusable" devices which allow the user to replace the syringe when the medicament has been used.

It is noted that whilst the term "syringe" is used herein for clarity and consistency, this term is not intended to be limiting. In some arrangements the syringe may for example be a cartridge (which, for example, may be arranged to receive a disposable needle) or other medicament container. In some arrangements the syringe/cartridge/medicament container may be formed integrally with the (or part of the) injection device.

Injection devices may, in addition to automating the delivery of the medicament, be arranged to automate the insertion of a needle into the skin prior to the delivery of the medicament.

Injection devices generally comprise a delivery arrangement which is arranged to automatically deliver a dose from the syringe, and optionally, to first displace the syringe within the housing to cause needle penetration. The delivery arrangement generally acts via a plunger which includes or engages a piston (also referred to as a "bung") which is slidably and sealably provided within the barrel of the syringe. The initial static friction or "stiction" between the bung and syringe resists forward movement of the piston relative to the syringe such that initially the delivery arrangement moves the syringe and piston forward into the needle insertion position. Here, further movement of the syringe is blocked and the delivery arrangement will continue to move forward, overcoming the stiction, and moving the piston and the bung through the syringe.

A common form of delivery arrangement includes an actuation mechanism which biases the plunger forwardly and a trigger mechanism which holds the plunger (directly or indirectly) against the force of the actuation mechanism until the trigger is released. For example the actuation mechanism may comprise a delivery actuator (for example a compression spring) which is held in an energised (or primed position) prior to release by the trigger. The trigger may be activated by a user's digit. Alternatively, the device may be pressure activated in which the trigger mechanism is provided by pressured contact with the injection site, typically via a needle shield.

An injection device is described in WO2016/189286. The actuation mechanism of this device comprises two springs, a first, relatively weak, insertion spring for moving the syringe through the device housing to insert the needle 14 into the skin and a second, relatively strong, delivery spring for driving the plunger 30 and piston through the syringe body in cooperation with the insertion spring. WO2016/189286 addresses a known problem with injection devices, namely that the force exerted by the insertion spring during the needle insertion phase may be great enough to damage the syringe when it bottoms out against the housing at the end of its travel. The problem is mitigated by incorporating a velocity regulator which limits the velocity of the syringe until it has bottomed out.

A further issue with known auto-injectors, particularly pressure activated devices, is that invariably some part of the actuating mechanism is required to extend rearwards from the syringe carrier to the delivery driving assembly which is located to the rear of the syringe. This requires various components to pass the syringe flange located at the end of the barrel. This inevitably results in an increase in the width of the device.

SUMMARY

According to a first aspect of the present invention there is provided an injection device for delivering a fluid from a syringe having a needle. The device comprises a casing, a syringe carrier located within a proximal end of the casing for receiving a syringe and being movable along a longitudinal axis of the device between a stowed position and a needle insertion position, and a drive assembly located within a distal end of the casing and being movable along said longitudinal axis by an insertion driver in order to move said syringe carrier and a loaded syringe from said stowed position to said needle insertion position.

The drive assembly in turn comprises an insertion tube having a proximal end abutting said syringe carrier or a loaded syringe, a firing cartridge comprising a plunger, a reaction assembly releasably coupled to the plunger, and a delivery driver coupled between the plunger and the reaction assembly, wherein the firing cartridge is configured to move forward with the insertion tube until the syringe carrier reaches said needle insertion position and then to continue moving in a proximal direction through the insertion tube until said plunger contacts or approaches a bung within the syringe, whereupon said plunger is released from the reaction assembly and the reaction assembly is pushed rearwards to latch onto the insertion tube and thereby provide a reaction surface against which the delivery driver can act in order to push the plunger forwards.

The device further comprises a first formation fixed relative to the casing and a second formation fixed relative to the insertion tube, the first and second formations defining between them a plurality of stop positions for the insertion tube relative to the casing, spaced along the direction of said longitudinal axis, to prevent significant rearward movement of the insertion tube along said axis when the plunger is released from the reaction assembly.

The first and second formations comprise respective sets of teeth configured to mesh together to define said plurality of stop positions. The first formation comprises one or more sets of projecting ribs, the ribs of each set defining, at their proximal ends, a set of helically arranged teeth. The teeth of the second formation may be provided at a distal end of the insertion tube. The device may be configured to bring the teeth of the first and second formations into mesh at a given one of said stop positions as a result of a rearward force exerted by the delivery driver on the insertion tube, via the reaction assembly.

The device may comprise an end cap fixed to a distal end of the outer casing, wherein said first formation is provided around an interior surface of the end cap. The insertion tube may be configured to perform a substantially helical movement within the casing in order to bring said first and second formations into alignment at one of said stop positions prior to the drive assembly completing movement of the syringe carrier and a loaded syringe to said needle insertion position. A substantially helical movement may be caused by engagement of a pin on one of the insertion tube and the end cap with a track on the other of the insertion tube and the end cap such that the pin follows the track during operation. The track may have a dog-leg shape.

The insertion driver and said delivery driver may comprise respective coil springs, wherein said coil springs are configured to store energy in compression and to release that energy by expansion.

According to a further aspect of the invention, there is provided an injection device for delivering a fluid from a syringe having a needle, the device comprising: a casing; a syringe carrier located within a proximal end of the casing for receiving a syringe and being movable along a longitudinal axis of the device between a stowed position and a needle insertion position, a drive assembly located within a distal end of the casing and being movable along said longitudinal axis by an insertion driver in order to move said syringe carrier and a loaded syringe from said stowed position to said needle insertion position, the drive assembly comprising an insertion tube having a proximal end abutting said syringe carrier or a loaded syringe, a firing cartridge comprising a plunger, a reaction assembly releasably coupled to the plunger, and a delivery driver coupled between the plunger and the reaction assembly, wherein the firing cartridge is configured to move forward with the insertion tube until the syringe carrier reaches said needle insertion position whereupon said plunger is released from the reaction assembly and the delivery driver can act in order to push the plunger forwards.

According to a further aspect of the present invention there is provided an injection device for delivering a fluid from a syringe having a needle. The device comprises a casing, a syringe carrier located within a proximal end of the casing for receiving a syringe and being movable along a longitudinal axis of the device between a stowed position and a needle insertion position, and a drive assembly located within a distal end of the casing and being movable along said longitudinal axis by an insertion driver in order to move said syringe carrier and a loaded syringe from said stowed position to said needle insertion position.

The drive assembly comprises an insertion tube having a proximal end abutting said syringe carrier or a loaded syringe, a firing cartridge comprising a plunger, a reaction assembly releasably coupled to the plunger, and a delivery driver coupled between the plunger and the reaction assembly, wherein the firing cartridge is configured to move forward with the insertion tube until the syringe carrier reaches said needle insertion position and then to continue moving in a proximal direction through the insertion tube until said plunger contacts or approaches a bung within the syringe, whereupon said plunger is released from the reaction assembly and the reaction assembly is pushed rearwards to latch onto the insertion tube and thereby provide a reaction surface against which the delivery driver can act in order to push the plunger forwards.

The device further comprises a clip or leaf spring located within a proximal end of the insertion tube and being in a partially compressed state, the plunger being configured to push the clip or leaf spring out of an end of the insertion tube at or close to an end of travel of the plunger, thereby allowing the clip or leaf spring to expand against an inner surface of the casing or a component coupled to the casing to produce an audible click.

According to a further aspect of the invention, there is provided an injection device for delivering a fluid from a syringe having a needle, the device comprising: a casing, a syringe carrier located within a proximal end of the casing for receiving a syringe and being movable along a longitudinal axis of the device between a stowed position and a needle insertion position, a drive assembly located within a distal end of the casing and being movable along said longitudinal axis by an insertion driver in order to move said syringe carrier and a loaded syringe from said stowed position to said needle insertion position, the drive assembly comprising an insertion tube having a proximal end abutting said syringe carrier or a loaded syringe, a firing cartridge comprising a plunger, a reaction assembly releasably coupled to the plunger, and a delivery driver coupled between the plunger and the reaction assembly, wherein the firing cartridge is configured to move forward with the insertion tube until the syringe carrier reaches said needle insertion position whereupon said plunger is released from the reaction assembly and the delivery driver can act in order to push the plunger forwards, the device further comprising a clip or leaf spring located within a proximal end of the insertion tube and being in a partially compressed state, the plunger being configured to push the clip or leaf spring out of an end of the insertion tube at or close to an end of travel of the plunger, thereby allowing the clip or leaf spring to expand against an inner surface of the casing or a component coupled to the casing to produce an audible click.

According to a further aspect of the present invention there is provided an injection device for delivering a fluid from a syringe having a needle. The device comprises a casing, a syringe carrier located within a proximal end of the casing for receiving a syringe, and a drive assembly located within a distal end of the casing. The drive assembly comprises an insertion tube, a firing cartridge comprising a plunger, and a delivery driver coupled to the plunger, wherein the firing cartridge is configured to move forward with the insertion tube until the syringe carrier reaches a needle insertion position, wherein the plunger is released. The device further comprises a biasing member such as a clip or leaf spring in a partially compressed state, the plunger being configured to release the clip or leaf spring, thereby allowing the clip or leaf spring to expand against an inner surface of the casing or other component of the injection device to produce an audible click.

The injection device may comprise an end of dose indicator comprising the biasing member.

Optionally, the end of dose indicator comprises a collar and wherein the biasing member is held in the partially compressed state within the collar.

Optionally, the biasing member is moveable relative to the collar. The biasing member may be moveable axially relative to the collar. Axial movement of the biasing member may move it out of a position retained by the collar, thereby releasing the biasing member.

Optionally, the collar comprises at least one aperture.

Optionally, the plunger is configured to engage the biasing member at the point on the delivery stroke such that further movement of the plunger on the delivery stroke causes the biasing member to move within the injection device.

Optionally, the further movement of the plunger on the delivery stroke causes the biasing member to be released from the partially compressed state.

Optionally, the biasing member comprises a C-shaped spring comprising free ends.

Optionally, the free ends of the C-shaped spring are configured to expand and impact the inner surface of the casing or other component of the injection device when the C-shaped spring is released.

Optionally, the end of dose indicator further comprises a rotational lock configured to prevent rotation of the biasing member relative to the collar.

Optionally, the biasing member is configured to expand radially.

BRIEF DESCRIPTION OF THE DRAWINGS

FIGS. 5a to 5f show longitudinal section views of a portion of a modified injection device;

DETAILED DESCRIPTION

In order to identify a potential problem that can be addressed by embodiments of the present invention, an injection device that may exhibit this problem will be described with reference to FIGS. 1 to 3.

Figure 1A:
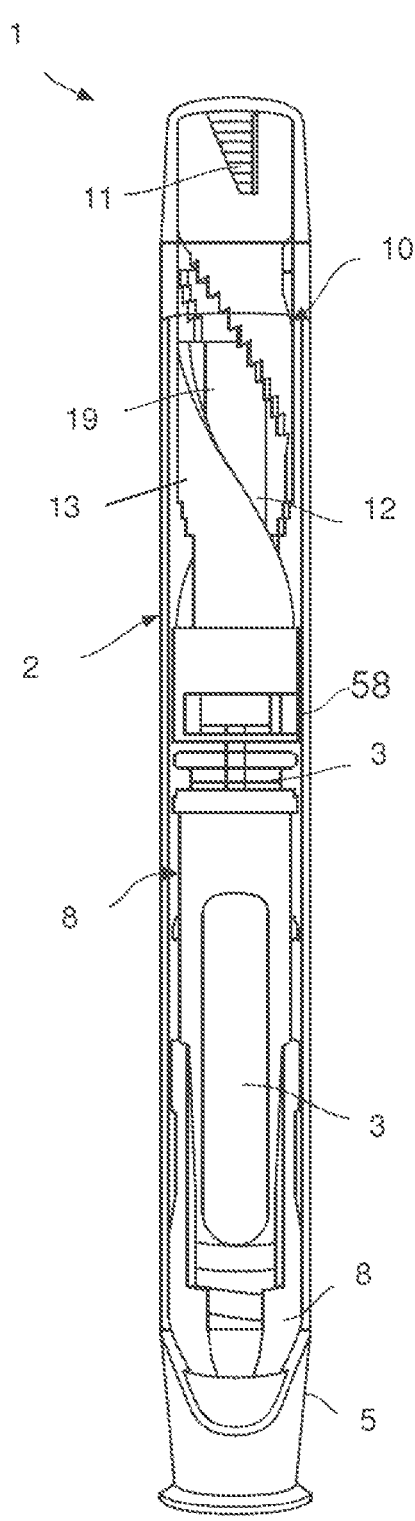
FIGS. 1a and 1b show a side view and longitudinal section of an injection device.
Figure 1B:
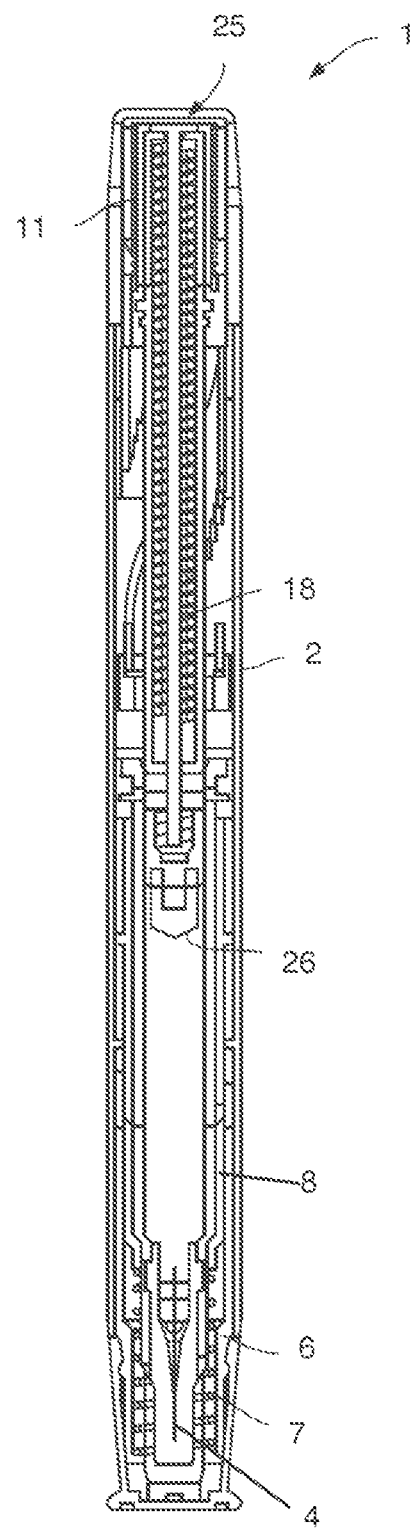

FIGS. 1a and 1b show respectively a side view and longitudinal section of this injection device 1 which, merely by way of example, is a one-time use device which may be disposed of after completion of an injection. The side view shows an outer casing 2 which is shown partially transparent to reveal certain of the inner workings of the injection device 1. The injection device includes a syringe 3 which comprises a needle 4 for insertion into an injection site for injection of a substance, typically a medicament. The injection device 1 may be considered automatic in that some of the injection operations require a single user operation and may be referred to as an auto-injector device, an auto-injector or an auto-injection syringe. In order to operate the device, the user removes a cap 5 at the proximal end of the device and which covers the needle 4. This action releases a needle shield 6 which is pushed forward by a shield drive spring 7 to cover the needle. The user then locates a suitable injection site and presses the needle shield 6 against the skin to activate the syringe.

Although not described in detail here, the device comprises a syringe carrier 8 within a lower portion of the casing 2 and within which the syringe barrel 9 is located. The syringe carrier is initially locked to the casing by an interlock (not shown). This interlock is released by pressure applied to the needle shield 6, allowing the syringe carrier and syringe to be driven forward to perform needle insertion.

Figure 2:
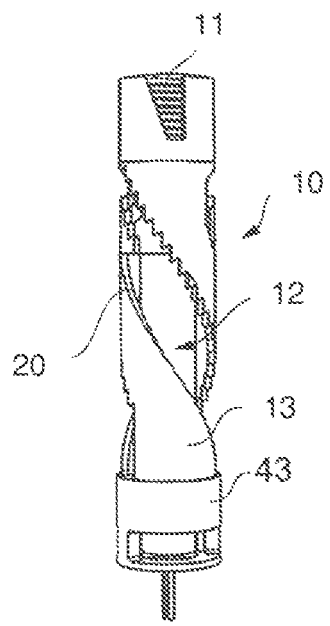
FIG. 2 shows a driving assembly of the device of FIG. 1.
Figure 3A:
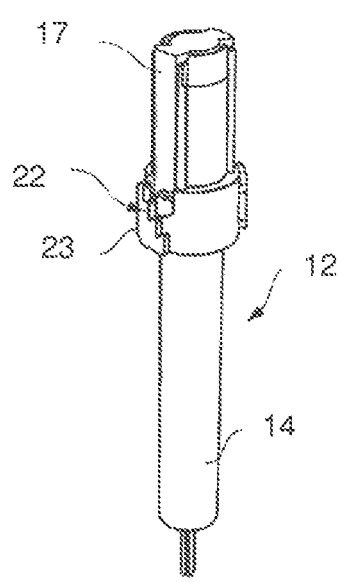
FIGS. 3a to 3c show constituent parts of the driving assembly as well as an insertion spring.
Figure 3B:
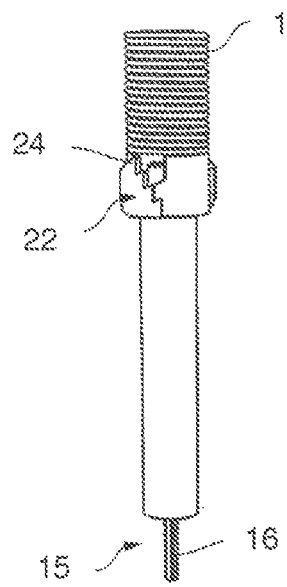
Figure 3C:
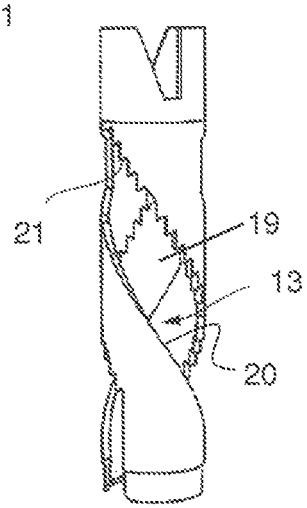

FIG. 2 shows in more detail a drive assembly 10 of the device 1 and which is loaded into the rear of the casing 2, behind the syringe 3, during assembly. The Figure also shows an insertion spring 11 that sits behind the drive assembly. This spring 11 is a relatively weak spring. When the device is fired, the insertion spring 11 pushes the entire drive assembly 10 forward, into the device. This action causes the syringe carrier 8 and syringe 3 to move forward, resulting in needle insertion. FIGS. 3a to 3c illustrate components of the drive assembly including a firing cartridge 12 and a generally cylindrical insertion tube 13, where the former is located concentrically within the latter. FIG. 2 further shows a component 43 (also pointed to generally by numeral 58 in FIG. 1a) located at the bottom of the insertion tube 13. This component may be integrated with the insertion tube or provided as a separate component.

The firing cartridge 12 comprises a cylindrical casing 14, referred to here as a "plunger", through which an elongate pin member 15 extends. An end 16 of the pin projects out of the bottom of the plunger 14 (optionally, a foot may be located on the end of the pin end 16 to provide more consistent contact with a variety of bung designs). The firing cartridge comprises a back assembly 17 that is detachably coupled to the rear of the plunger 14. As best seen in FIG. 1b, a relatively strong delivery spring 18 is located between the back assembly 17 and the plunger 14 such that the top of the delivery spring 18 pushes against the inside of the back assembly, whilst the bottom of the delivery spring pushes against the bottom of the plunger 14. Of course, as long as the back assembly and plunger are connected, the delivery spring 18 cannot expand.

Considering further the insertion tube 13, this is provided with a helical channel 19, the lower surface 20 of which is generally smooth, with the upper surface being provided with ratchet teeth 21 extending along substantially the entire length of the channel 19. In the assembled drive assembly 10, a part 22 of the back assembly 17 projects through the helical channel 19. A lower surface 23 of the projecting part, opposed to the lower surface 20 of the insertion tube channel 19, has a smooth finish, whilst an upper surface, opposed to the ratchet teeth 21 of the channel, is provided with a set of complimentary teeth 24.

Operation of the injection device 1 will now be described with reference to FIGS. 4a to 4i which show sections of the injection device in various states.

Figure 4A:
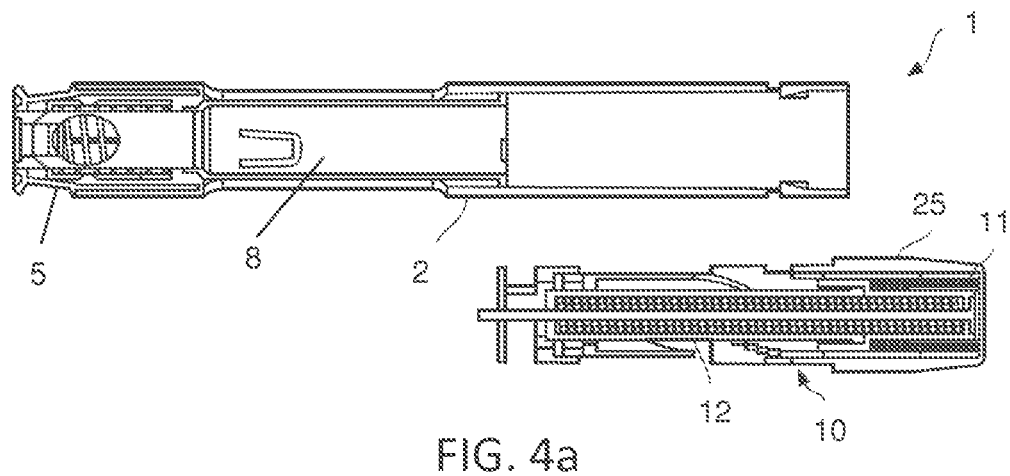
FIGS. 4a to 4i show longitudinal section views of the injection device of FIG. 1 prior to final assembly and at various operational stages.
Figure 4B:
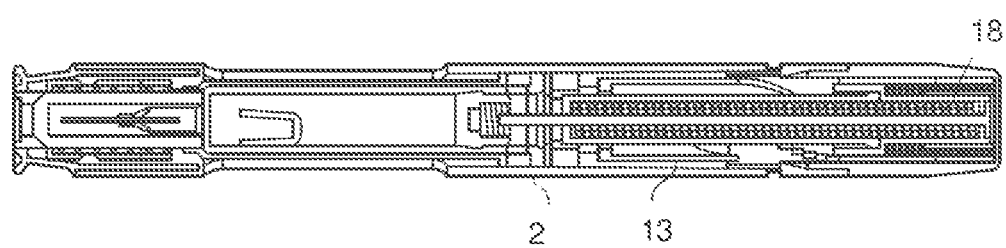

FIG. 4a shows the outer casing 2 containing a front assembly (including the needle shield 6 and syringe carrier 8), with a syringe 3 loaded into the front assembly. The Figure also shows the drive assembly 10 having an end cap 25 located around one end and with the insertion spring 11 acting between the end cap and the drive assembly. The end cap 25 is fixed to the casing 2 in the assembled device. FIG. 4b shows the assembled device, with the insertion tube 13 pushed rearwards by the barrel and/or syringe carrier to disengage a drive assembly retaining latch (not shown) which holds the drive assembly 10 together prior to assembly. In this state, the forward end of the insertion tube 13 is in contact with the rear end of the syringe barrel 9.

Figure 4C:
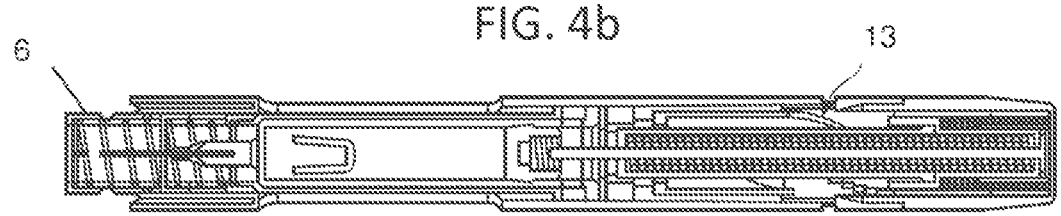
Figure 4D:
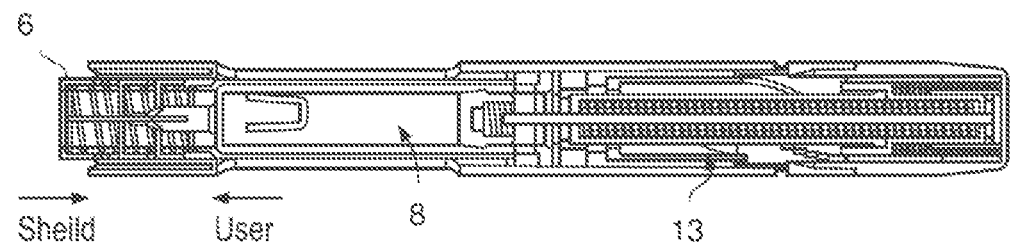

FIG. 4c shows the cap 5 removed and the shield 6 deployed ready for location of an injection site. FIG. 4d shows the beginning of the activation stroke in which the shield 6 is depressed into the outer casing 2 by the user applying pressure on the outer casing 2 towards the injection site. This action releases the interlock securing the syringe carrier 8 to the casing 2, allowing the insertion spring 11 to expand. This pushes the drive assembly 10 forward, which in turn pushes the syringe and the syringe carrier forward. [NB. The insertion spring 11 is stronger than the shield drive spring 7, causing the latter to be re-compressed during this stage of operation, both limiting the insertion force applied to the needle and preparing the spring for later redeployment of the needle shield 6.]

Although not clearly shown in the Figures, the end cap 25 is provided with two pairs of legs that extend into the casing. These engage respectively with tracks provided in the insertion tube 13 and the firing cartridge 12 and act as anti-rotation features. During the initial expansion of the insertion spring 11 and forward movement of the drive assembly 10, neither the insertion tube 13 nor the firing cartridge 12 can rotate within the housing.

Figure 4E:
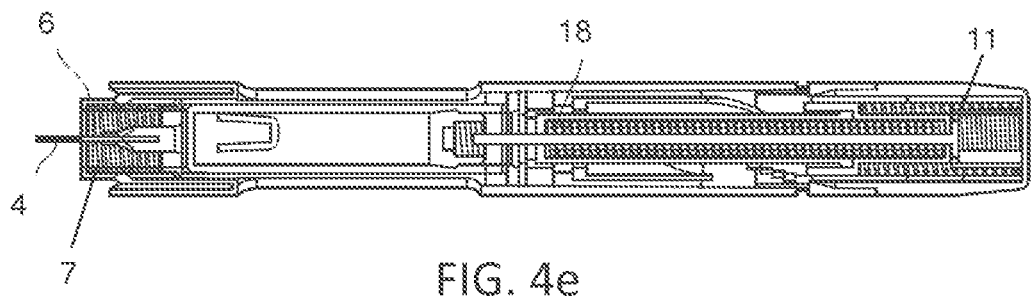

Forward movement of the syringe carrier 8 is stopped when features on the carrier engage with stop features on the inside of the casing 2. Just before this position is reached, the anti-rotation features that prevent rotation of the insertion tube 13 are released. The anti-rotation features on the firing cartridge 12 remain engaged. FIG. 4e shows the syringe and its needle in the fully inserted position.

At this stage of the operation, further forward movement of the insertion tube 13 is blocked. However, as the anti-rotation features are now released, the insertion tube can rotate. It does so as a result of the forward force exerted by the lower surface 23 of the projecting part 22 (of the firing cartridge) against the lower surface 20 of the helical channel 19 (of the insertion tube). In other words, the insertion tube rotates within the casing as the firing cartridge continues its forward movement through the casing (in a helical manner with respect to the insertion tube). However, this rotation of the insertion tube 13 is stopped when a stop feature on the top of the insertion tube engages a stop formed in the cap. In total, the insertion tube may rotate by only a relatively small amount, e.g. 15 degrees or so. This rotation also brings the stop feature on the insertion tube underneath a further stop formed in the cap, preventing any backward movement of the insertion tube within the outer casing 2.

Figure 4F:
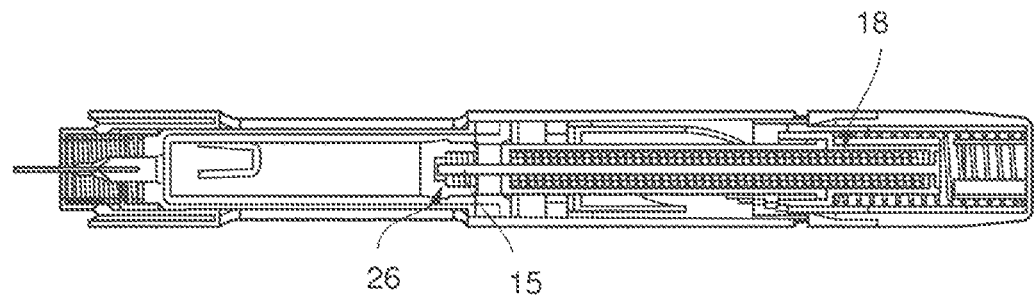
Figure 4G:
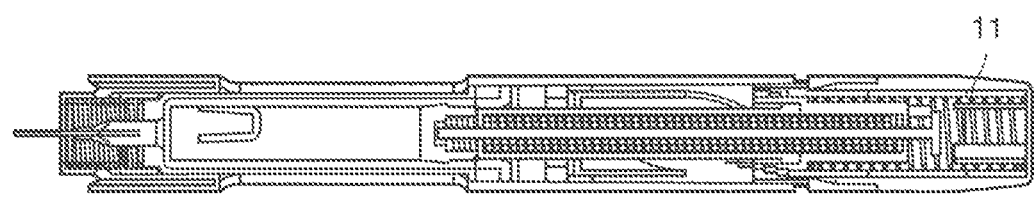

At the point where the stop feature on the insertion tube 13 has been rotated under the stop in the end cap, preventing further rotation and rearward movement of the insertion tube, the anti-rotation features on the firing cartridge 12 now run out, allowing the firing cartridge to rotate within the insertion tube 13 and therefore continue its forward axial motion through the insertion tube. FIG. 4f shows completion of the forward motion of the intact firing cartridge 12, at which point the end 16 of the pin member 15 hits the bung 26 within the syringe barrel 9. The resistance presented by the bung now causes the pin to push back against the back assembly 17. A release mechanism causes the back assembly to decouple from the plunger 14. This position is illustrated in FIG. 4g.

The delivery spring 18 now begins to expand. Due to the relatively high frictional resistance between the bung 26 and the inside of the syringe barrel 9, the delivery spring first pushes the back assembly 17 towards the end cap 25. Almost immediately however, the teeth 24 on the projecting part of that back assembly (best seen in FIG. 3b) encounter the ratchet teeth 21 provided on the upper surface of the helical channel of the insertion tube. As the insertion tube cannot now move rearwards, further rearward movement of the back assembly 17 is prevented. The full force of the delivery spring 18 now acts on the plunger 14 and therefore on the bung 26, causing medicament to be ejected from the syringe barrel through the needle. It will be appreciated that the use of a firing cartridge 12 which is moved through the casing in its entirety during needle insertion ensures that almost the full force of the delivery spring is available for delivering the medicament. The ratchet mechanism provided between the insertion tube 13 and the back assembly 17 ensures that the back assembly is locked in place with minimal rearward movement upon release of the delivery spring. Moreover, by allowing a decoupling of the firing cartridge from the insertion tube upon completion of the needle insertion phase, the relatively weak insertion spring can be used to continue the forward movement of the firing cartridge to close the gap between the plunger and the bung before the delivery spring is released. This avoids having to use the delivery spring for this purpose which could result in damage to the device due to the high force generated by the delivery spring.

Figure 4H:
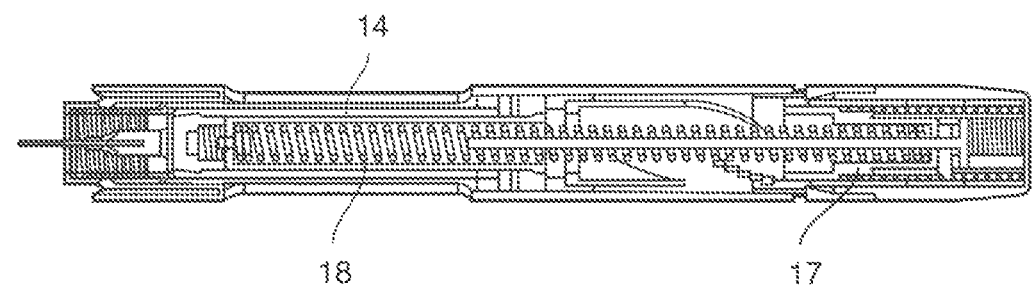
Figure 4I:
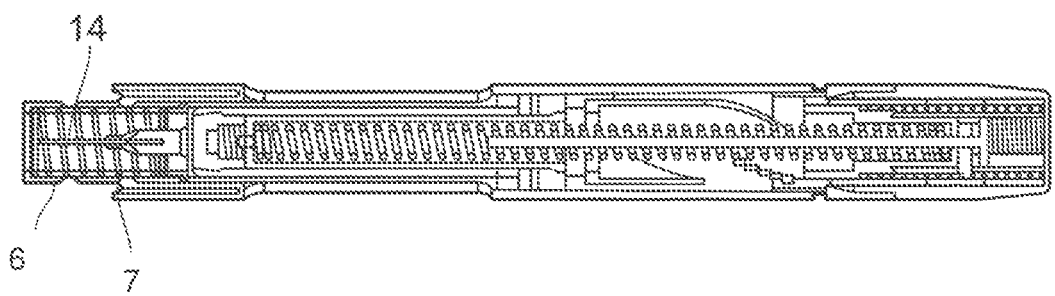

FIG. 4h illustrates the state of the device following complete delivery. The user can now release the pressure on the skin. As this happens, the shield drive spring 7 is able to push the needle shield 6 in a proximal direction to recover the needle 4. Lockout features may be provided to lock the needle shield in this fully deployed position. This locked-out state is shown in FIG. 4i.

FIGS. 5a to 5f illustrate a part of an injection device that operates in a similar way to the device described above, but which replaces the helical channel 19 of the insertion tube 13 with a pair of longitudinally extending channels 27 (only one of which is shown in the drawings). The insertion tube 13 comprises two rearwardly extending legs 28a, 28b which define the channels therebetween, with teeth 29a, 29b along both sides of each channel. The back assembly 17 is modified to provide a pair of projecting parts 30 which project through respective channels of the insertion tube. Each projecting part is provided with a set of teeth 31a, 31b on each side.

FIG. 5a illustrates the drive assembly at the point where the insertion tube 13 has just reached the end of its travel, i.e. the syringe carrier has bottomed out in the casing and needle insertion is complete. Here, the anti-rotation features on the insertion tube 13 are disengaged. The firing cartridge 12, which still cannot rotate, continues to be pushed forward by the insertion spring 11 acting on the back assembly 17. This causes the back assembly, and therefore the entire firing cartridge 12, to move in a zig-zag fashion, relative to the insertion tube, as the teeth 31a, 31b of the projecting parts 30 move over the opposed teeth 29a, 29b of the longitudinal channels. FIGS. 5b to 5e illustrate this forward movement, i.e.

FIG. 5b—Firing Assemble Slides into Zig Zag Track
FIG. 5c—Firing Assembly 'Zig Zags' Down Track
FIG. 5d—Plunger Released
FIG. 5e—Teeth Engaged.
FIG. 5f—End of Drug Delivery.

As described above with respect to FIGS. 1 to 4, when the end 16 of the pin member 15 hits the bung 26, the back assembly 17 is disengaged from the plunger 14. The expansion of the delivery spring 18 causes the projecting part 22 of the back assembly 17 to push back against the insertion tube 13 which cannot itself move back. The shape of the teeth on the projecting parts and the longitudinal channel in the insertion tube quickly stop any further rearward movement of the back assembly 17. As with the first described device, this allows the full force of the delivery spring 18 to be applied to the plunger 14.

In the injection devices described above, and in devices featuring similar mechanisms, it is desirable to minimise movement of all components, other than the plunger 14, due to expansion of the delivery spring 18 in order to minimise the risk of device failure. As already noted, the device described above helps to minimise any rearward movement of the firing cartridge 12 within the insertion tube 13 when the delivery spring 18 is released. However, these devices potentially allow a small rearward movement of the insertion tube, and with it the firing cartridge, when the delivery spring is released. This can arise as a result of manufacturing tolerances and the need to allow for such tolerances. In particular, a gap of as much as 4 mm may be present between the features on the insertion tube and the end cap which are intended to block rearward movement of the insertion tube at the end of the needle insertion phase. This means that there is a significant distance over which the delivery spring can accelerate the insertion tube prior to the full force of the delivery spring being applied to the plunger.

This problem can be mitigated by implementing a mechanism between the insertion tube 13 and the end cap 25 which uses a principle similar to that already used to prevent rearward movement of the firing cartridge 12 within the insertion tube 13.

For ease of explanation, an entire device will not be described here. Rather, the skilled person will appreciate that much of the improved device is common to the devices described with reference to FIGS. 1 to 5, and specifically the device of FIG. 5 which relies upon a pair of longitudinally extending channels to restrict backward movement of the firing cartridge 12 within the insertion tube when the delivery spring 18 is released.

Figure 6:
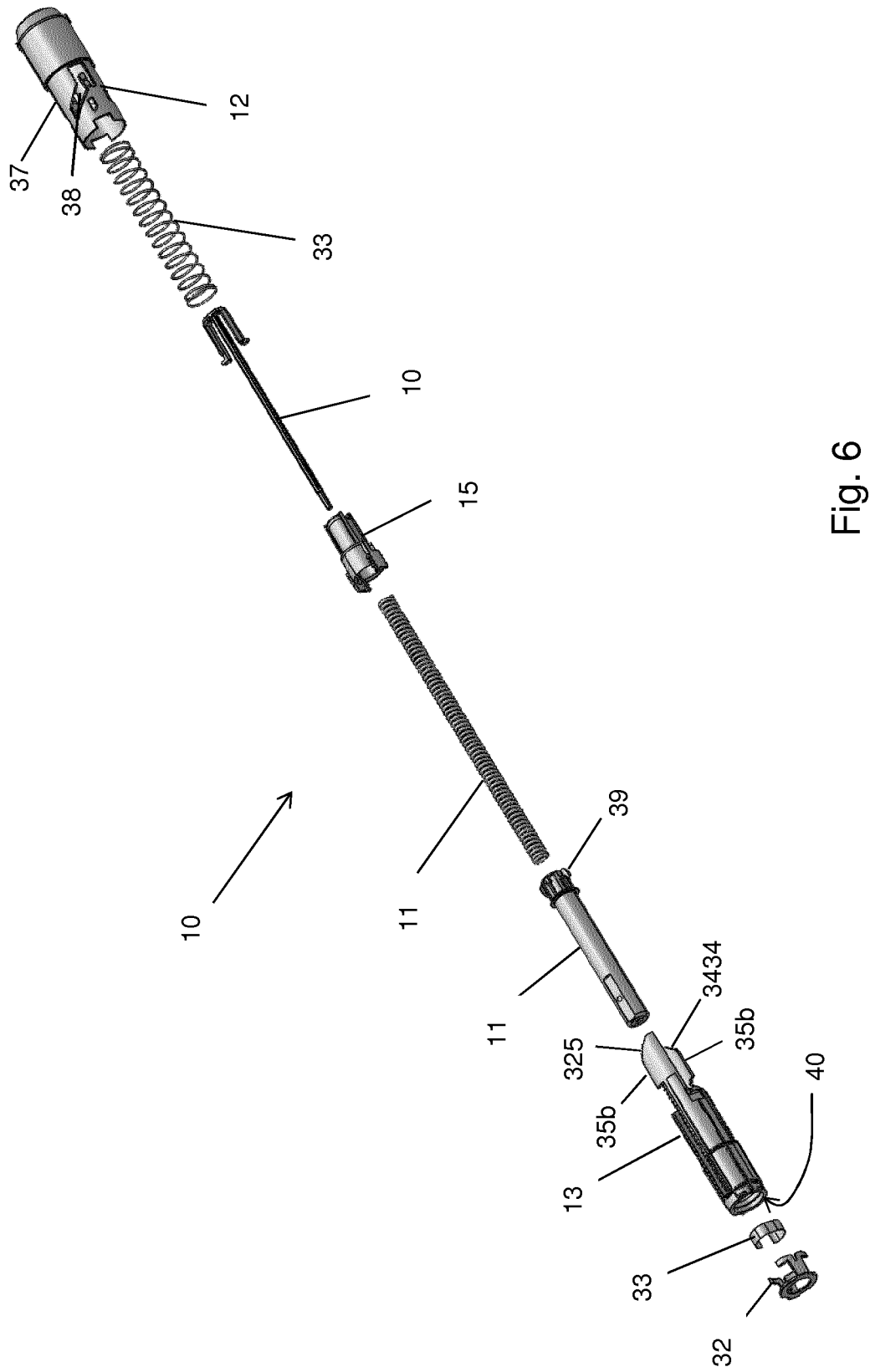
FIG. 6 shows an exploded view of a drive assembly, insertion spring and end cap of an injection device according to an exemplary embodiment of the present invention.

FIG. 6 is an exploded view of a modified drive assembly 10 along the axis of insertion and delivery, where components are identified using numerals used above with reference to FIGS. 1 to 5. Additional components are also shown, namely an insertion tube base 32 (previously part of the insertion tube) and an end of dose click spring, C-shaped spring, leaf spring or clip, 33.

FIGS. 7a to 7d illustrate features designed to limit rearward movement of the insertion tube 13 as a result of release of the delivery spring 18, assuming that the design of FIG. 5 is employed (although it is equally applicable to other designs including that of FIGS. 1 to 4). The anti-rotation features provided on the inner surface of the end cap 25 are replaced with two sets of four ribs 36 on that inner surface, only one of which sets is visible in the Figure. The ribs 36 of each set increase in length in a clockwise direction (when viewing the device end on from the top). The lowermost end of each rib is angled slightly. As perhaps best seen in conjunction with the exploded view of FIG. 6, both ends of the top of the insertion tube are provided with angled stop surfaces 34a, 34b on which are formed complimentary sets of teeth. Both ends are also provided with longitudinally extending stop surfaces 35a, 35b continuing below the angled stop surfaces.

Figure 7A:
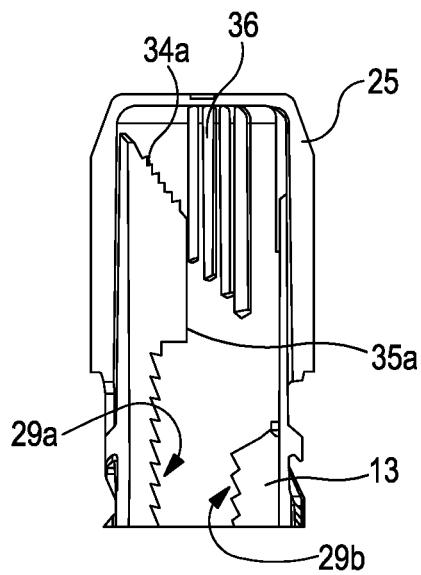
FIGS. 7a to 7d shows longitudinal section views of an end portion of the injection device of FIG. 7 in various operational stages.
Figure 7B:
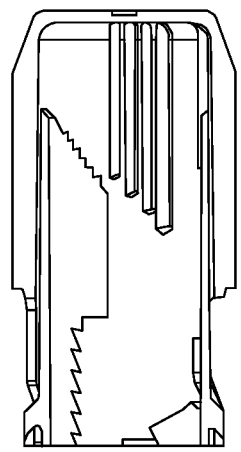

FIG. 7a illustrates the orientation of the end cap 25 and the top of the insertion tube 13 following assembly and prior to operation of the device. It will be appreciated that the leftmost rib 36 formed on the inner surface of the cap 25 is blocking rotation of the insertion tube 13 in one direction due to its abutment against the stop surface 35a. A rib of the other of the pair of ribs 36 similarly blocks rotation of the insertion tube 13 in the other direction. Upon firing of the device, as described above, the entire drive assembly 10 begins to move forward through the outer casing 2. During a first part of this travel, the insertion tube 13 is prevented from rotating by engagement with the shortest of the ribs 36. Of course, during this travel, the firing cartridge 12 is also prevented from rotating.

Figure 7C:
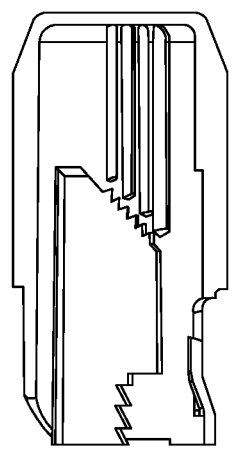
Figure 7D:
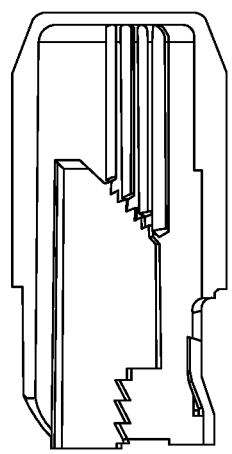

With reference to FIG. 6, it will be seen that the skirt 37 of the end cap 25 is provided with a dog-leg shaped track 38 that initially follows a longitudinal path (from the top of the cap) and which then deviates at an angle. This track is engaged by a pin 39 provided on an outer surface of the insertion tube 13. The shortest rib of each set of ribs 36 is of a length such that the longitudinally extending stop surfaces 35a, 35b of the insertion tube pass over their ends at some point before the insertion tube bottoms out. This is the position shown in FIG. 7b. This coincides with the pin 39 moving from the straight to the angled section of the track 38. Further forward movement of the drive assembly 10 causes it to rotate within the end cap 25 and the casing 2. The angled stop surfaces 34a, 34b of the insertion tube are caused to move under and along the respective sets of ribs 30, moving at an angle that matches the angle of alignment of the lower ends of the ribs. The angled stop surface therefore remains close to, but slightly spaced apart from, the ends of the ribs (e.g. 0.1 to 0.5 mm) at all points in the forward helical motion of the drive assembly, including when the insertion tube bottoms out. This state of the end of the device when the insertion tube bottoms-out is shown in FIG. 7c.

The anti-rotation features preventing rotation of the firing cartridge 12 run out just before the insertion tube bottoms out, meaning that the cartridge can move down through the insertion tube in a zig-zag manner as discussed upon. When the pin end 16 of the pin member 15 hits the bung 28 within the syringe barrel, the back assembly 17 is released from the insertion tube 13, causing the back assembly to be pushed back by the delivery spring 18. This locks the teeth on the projecting parts of the back assembly against the teeth formed along the longitudinal tracks of the insertion tube. This in turn pushes the insertion tube 13 rearwards, pushing the teeth of the angled stop surfaces 34a, 34b against the angled ends of the ribs 30. As already noted, this backward movement of the insertion tube 13 within the casing 2 is relatively small, typically 0.5 mm or so. The delivery spring 18 therefore has little distance over which to accelerate the insertion tube, minimising the possibility of damage.

Figure 8A:
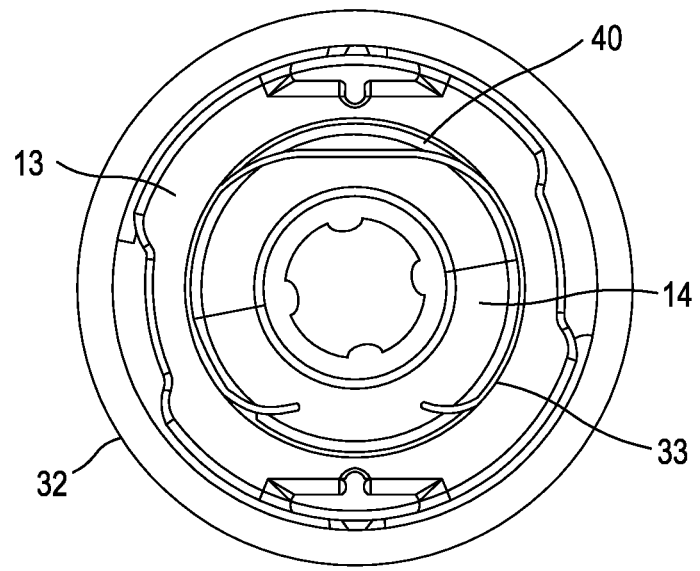
FIGS. 8a and 8b illustrates an audible click feature of the device of FIG. 6.
Figure 8B:
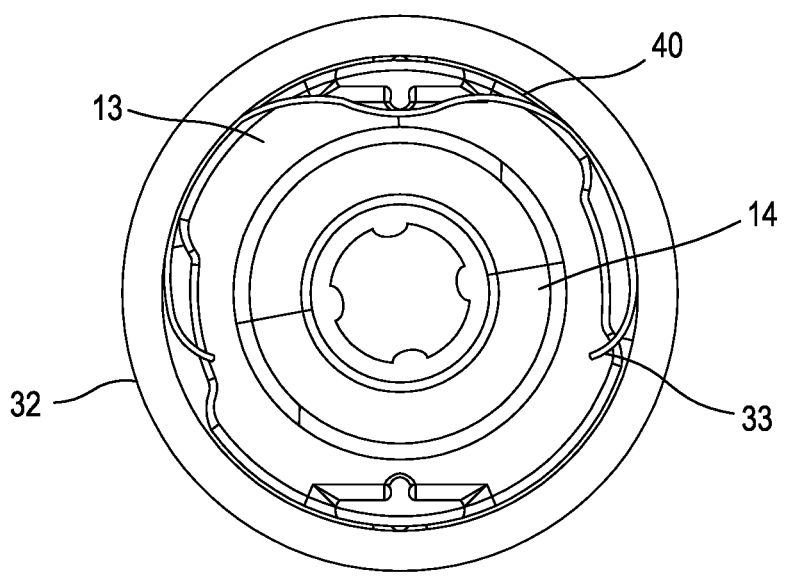

Reference has already been made to the end of dose click spring, leaf spring, C-shaped spring or clip 33 (see FIG. 6). This spring is a metal ring comprising a cut-out section and is fitted into a recess 40 formed in the proximal end of the insertion tube 13. The spring is compressed during fitting and is located behind an insertion tube base 32 that closes the proximal end of the insertion tube. When the plunger 14 of the firing mechanism reaches the end of the delivery stroke, a feature formed on an outer surface of the plunger pushes the click spring out of the end of the insertion tube, allowing it to expand out between legs of the insertion tube base and impact on an inner face of the outer casing, causing an audible click. This is illustrated in FIGS. 8a and 8b which show an end on view of the drive assembly before and after release of the click spring.

Figure 9:
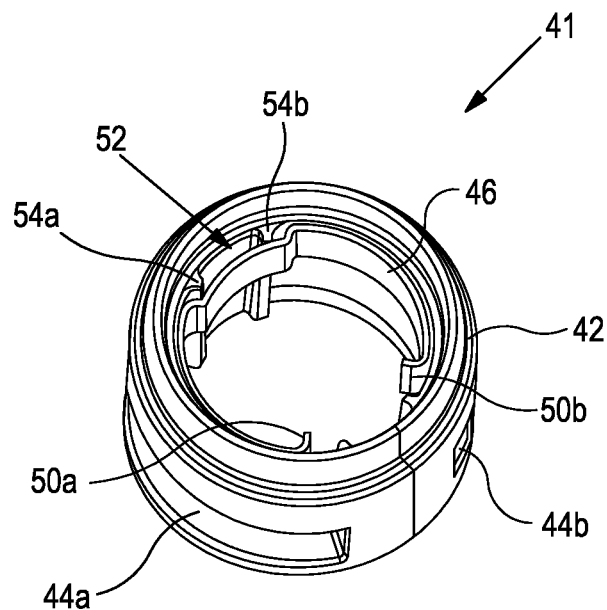
FIG. 9 shows an exemplary end of dose indicator.

FIG. 9 shows a perspective view of an end of dose indicator 41. The end of dose indicator 41 may be configured to provide an indication that substantially all of a substance contained within the barrel 9 of the syringe has been expelled from the barrel 9. The indication may be provided at the end of the delivery stroke of the plunger 14, or slightly before the end of the delivery stroke of the plunger 14. The delivery stroke of the plunger 14 may encompass movement of the plunger to expel the substance contained within the barrel 9, and the end of the delivery stroke may encompass the point at which the plunger 14 has expelled substantially all of the substance within the barrel 9, or substantially all of a predetermined amount of the substance within the barrel 9.

The end of dose indicator 41 may comprise a collar 42. The collar 42 may comprise at least one aperture 44. The at least one aperture 44 may be in a sidewall of the collar 42. The end of dose indicator includes a biasing member 46, which may be the end of dose click spring 33 described above. In exemplary arrangements, the biasing member 46 may be a c-shaped spring or a leaf spring. In some arrangements, the collar 42 may comprise the insertion tube base 32 described above.

The biasing member 46 may be received within the collar 42 and moveable with respect to the collar 42. In the exemplary end of dose indicator shown in FIG. 9, the biasing member 46 may be axially moveable with respect to the collar 42. In some exemplary arrangements, the biasing member 46 is not rotatable relative to the collar 42. In alternative arrangements, the biasing member 46 may be rotatable with respect to the collar, or may be both axially moveable and rotatable with respect to the collar 42.

The collar 42 may be configured to hold the biasing member 46 in a primed, or partially compressed, state. The biasing member 46 may be configured to expand to provide an end of dose indication when the biasing member 46 enters the at least one aperture 44. In exemplary arrangements, the expansion of the biasing member 46 may be radial expansion, which may be outward radial expansion. In other arrangements, the biasing member 46 may expand if it is moved axially such that it exits an upper or lower end of the collar 42. In general, the biasing member 46 expands when it is released from being restrained by the collar 42.

In exemplary arrangements, the aperture 44 may be configured such that when the biasing member is longitudinally aligned with the aperture 44, the biasing member 46 expands into the aperture 44 and impacts a component of the injector device to provide an audible end of dose indication to the user. In exemplary arrangements, the biasing member 46 may expand and impact an inner surface of the outer casing of the injector device.

The exemplary collar 42 shown in FIG. 9 comprises two apertures 44a, 44b. The apertures 44a, 44b are angularly spaced about a longitudinal axis of the collar 42. In the collar 42 of FIG. 9, the apertures 44a, 44b are equally spaced about the longitudinal axis. The skilled person will appreciate that any number of apertures may be used in alternative arrangements, providing the biasing member 46 is allowed to expand therein to impact a surface of the injector device.

In alternative arrangements, the collar 42 may not comprise an aperture. In such arrangements, the biasing member may be held in the primed state within the collar 42 and may exit the collar 42 at substantially the end of the delivery stroke to expand and provide the indication by impacting a component of the injection device.

In the exemplary end of dose indicator shown in FIG. 9, the biasing member 46 comprises a spring comprising free ends 50a, 50b. The spring may be C-shaped. In the primed state, the free ends 50a, 50b of the biasing member 46 are compressed towards one another. When the biasing member 46 is brought into alignment with the apertures 44a, 44b (or exits an end of the collar 42), the free ends 50a, 50b are able to expand away from one another and enter the corresponding apertures 44a, 44b. The apertures 44a, 44b may be configured such that entry of the free ends 50a, 50b of the biasing member 46 into the corresponding apertures 44a, 44b, cause the free ends 50a, 50b to expand and impact another component of the injector device to provide an audible indication to the user. In exemplary arrangements, the free ends 50a, 50b may expand and impact an inner surface of the outer casing of the injector device.

Exemplary collars 42 may comprise a rotational lock 52 configured to prevent rotation of the biasing member 46 with respect to the collar 42. The exemplary rotational lock 52 of FIG. 9 comprises ribs 54a, 54b. The ribs extend axially along a radially inner surface of the collar 42. The ribs 54a, 54b interact with a surface of the biasing member 46 to prevent rotation of the biasing member 46 within the collar 42. In such arrangements, the ribs 54a, 54b may be further configured to guide the axial movement of the biasing member 46 within the collar 42.

The rotational lock 52 may also, or alternatively, be configured to ensure that biasing member 46 is received within the collar 42 in the correct orientation. In exemplary arrangements, the correct orientation of the biasing member is such that free ends 50a, 50b of the biasing member 46 are angularly aligned with the apertures, 42a, 42b. The free ends 50a, 50b may be angularly aligned with the apertures 42a, 42b such that axial movement of the biasing member 46 without rotation, allows the free ends 50a, 50b to enter the corresponding apertures 42a, 42b.

Operation of the end of dose indicator is now described with reference to FIGS. 10a and 10b.

Figures 10A, 10B:
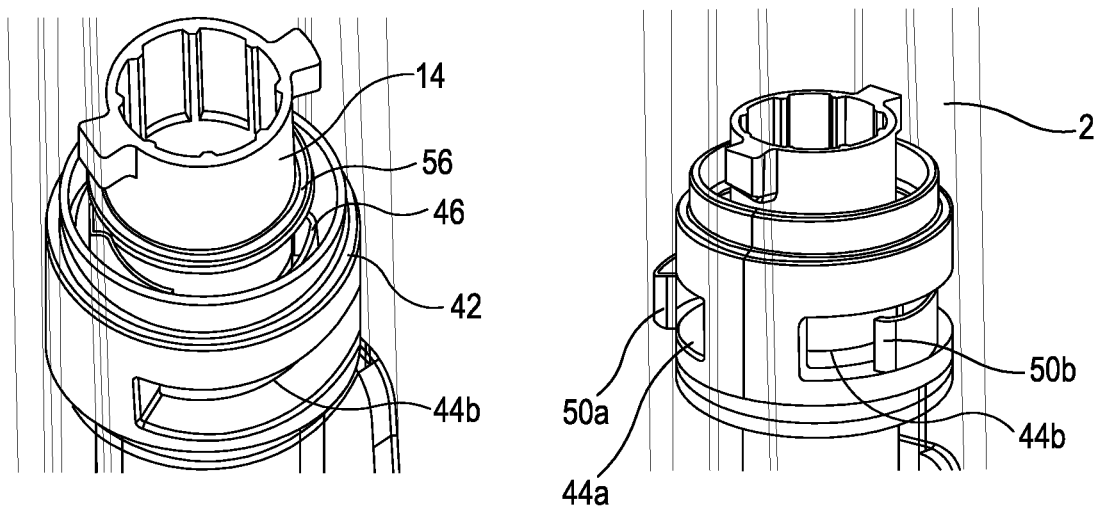
FIGS. 10a and 10b show the exemplary end of dose indicator of FIG. 9 at different operational stages.

FIG. 10a shows the end of dose indicator prior to the plunger 14 reaching the end of the delivery stroke. The biasing member 46 is held in a primed, or partially compressed state, within the collar 42. The plunger 14 is received within the collar 42 and the biasing member 46 and is axially moveable on a delivery stroke relative to the collar 42 and the biasing member 46.

The plunger 14 is configured to couple to the biasing member 46 at a point on the delivery stroke such that movement of the plunger 14 on the delivery stroke causes movement of the biasing member. In the exemplary arrangement shown in FIGS. 10a and 10b, a flange 56 formed on an outer surface of the plunger 14 engages the biasing member 46 to couple the plunger 14 and the biasing member 46. The skilled person will appreciate that in alternative arrangements, projections or other features formed on the plunger 14 may be utilised to engage the biasing member 46 and couple the biasing member 46 and the plunger 14.

As described above, rotation of the biasing member 46 when the biasing member is coupled to the plunger 14 is prevented by the rotational lock 46. The biasing member 46 therefore moves axially with the plunger rod on the delivery stroke without rotation.

The biasing member 46 may move on the delivery stroke with the plunger 14 until the biasing member 46 is aligned with the apertures 44a, 44b. The biasing member 46 may enter the aperture 44a, 44b and expand to impact a component of the injection device. In the exemplary arrangement shown in FIGS. 10a and 10b, the biasing member 46 moves on the delivery stroke with the plunger 14 until free ends 50a, 50b of the biasing member 46 align with corresponding apertures 44a, 44b. The free ends 50a, 50b enter the corresponding apertures 42a, 42b which causes the free ends 50a, 50b to expand and impact a component of the injection device. In the exemplary arrangement of FIGS. 10a and 10b, the free ends 50a, 50b impact the inner face of the outer casing 2 of the injection device.

In exemplary arrangements, the biasing member 46, or the free ends 50a, 50b, may be configured to enter the apertures 42a, 42b at substantially the end of the delivery stroke of the plunger 14.

The end of dose indicator 41 may be utilised with substantially any of the features and components described above.

The skilled person will be able to envisage other embodiments of the invention without departing from the scope of the appended claims. The specific description provided above is one way of implementing the invention and should not be considered limiting.

The invention claimed is:

1. An injection device for delivering a fluid from a syringe having a needle, the device comprising:
   a casing;
   a syringe carrier located within a proximal end of the casing for receiving a syringe and being movable along a longitudinal axis of the device between a stowed position and a needle insertion position:
   a drive assembly located within a distal end of the casing and being movable along said longitudinal axis by an insertion driver in order to move said syringe carrier and the syringe from said stowed position to said needle insertion position, the drive assembly comprising
      an insertion tube having a proximal end abutting said syringe carrier or the syringe,
      a firing cartridge comprising a plunger, a reaction assembly releasably coupled to the plunger, and a delivery driver coupled between the plunger and the reaction assembly, wherein the firing cartridge is configured to move forward with the insertion tube until the syringe carrier reaches said needle insertion position and then to continue moving in a proximal direction through the insertion tube until said plunger contacts or approaches a bung within the syringe, whereupon said plunger is released from the reaction assembly and the reaction assembly is pushed rearwards to latch onto the insertion tube and thereby provide a reaction surface against which the delivery driver can act in order to push the plunger forwards,
   the device further comprising a first formation fixed relative to the casing and a second formation fixed relative to the insertion tube, the first and second formations defining between them a plurality of stop positions for the insertion tube relative to the casing, spaced along the direction of said longitudinal axis, to prevent significant rearward movement of the insertion tube along said axis when the plunger is released from the reaction assembly.

2. An injection device according to claim 1, wherein said first and second formation comprise respective sets of teeth configured to mesh together to define said plurality of stop positions.

3. An injection device according to claim 2, wherein said first formation comprises one or more sets of projecting ribs, the ribs of each set defining, at their proximal ends, a set of helically arranged teeth.

4. An injection device according to claim 2, wherein the teeth of the second formation are provided at a distal end of the insertion tube.

5. An injection device according to claim 2, wherein the device is configured to bring the teeth of the first and second formations into mesh at a given one of said stop positions as a result of a rearward force exerted by the delivery driver on the insertion tube, via the reaction assembly.

6. An injection device according to claim 1 and comprising an end cap fixed to a distal end of the outer casing, wherein said first formation is provided around an interior surface of the end cap.

7. An injection device according to claim 1, wherein the insertion tube is configured to perform a substantially helical movement within the casing in order to bring said first and second formations into alignment at one of said stop positions prior to the drive assembly completing movement of the syringe carrier and the syringe to said needle insertion position.

8. An injection device according to claim 6, wherein said first and second formation comprise respective sets of teeth configured to mesh together to define said plurality of stop positions,
   wherein the device is configured to bring the teeth of the first and second formations into mesh at a given one of said stop positions as a result of a rearward force exerted by the delivery driver on the insertion tube, via the reaction assembly, and
   wherein said substantially helical movement is caused by engagement of a pin on one of the insertion tube and the end cap with a track on the other of the insertion tube and the end cap such that the pin follows the track during operation.

9. An injection device according to claim 8, wherein said track has a dog-leg shape.

10. An injection device according to claim 1, wherein said insertion driver and said delivery driver comprise respective coil springs.

11. An injection device according to claim 10, wherein said coil springs are configured to store energy in compression and to release that energy by expansion.

12. An injection device according to claim 1, further comprising a clip located within a proximal end of the insertion tube and being in a partially compressed state, the plunger being configured to push the clip out of an end of the insertion tube at or close to an end of travel of the plunger, thereby allowing the clip to expand against an inner surface of the casing or a component couple to the casing to produce an audible click.

13. An injection device for delivering a fluid from a syringe having a needle, the device comprising:
   a casing;
   a syringe carrier located within a proximal end of the casing for receiving a syringe and being movable along a longitudinal axis of the device between a stowed position and a needle insertion position:
   a drive assembly located within a distal end of the casing and being movable along said longitudinal axis by an insertion driver in order to move said syringe carrier and the syringe from said stowed position to said needle insertion position, the drive assembly comprising
      an insertion tube having a proximal end abutting said syringe carrier or the syringe,
      a firing cartridge comprising a plunger, a reaction assembly releasably coupled to the plunger, and a delivery driver coupled between the plunger and the reaction assembly, wherein the firing cartridge is configured to move forward with the insertion tube until the syringe carrier reaches said needle insertion position and then to continue moving in a proximal direction through the insertion tube until said plunger contacts or approaches a bung within the syringe, whereupon said plunger is released from the reaction assembly and the reaction assembly is pushed rearwards to latch onto the insertion tube and thereby provide a reaction surface against which the delivery driver can act in order to push the plunger forwards, the device further comprising a clip located within a proximal end of the insertion tube and being in a partially compressed state, the plunger being configured to push the clip out of an end of the insertion tube at or close to an end of travel of the plunger, thereby allowing the clip to expand against an inner surface of the casing or a component couple to the casing to produce an audible click.

14. An injection device according to claim 13, wherein the clip comprises a leaf spring or c-shaped spring.

15. An injection device according to claim 14, wherein the leaf spring or c-shaped spring comprises free ends, and wherein the free ends are configured to expand radially.

16. An injection device according to claim 13, wherein the plunger comprises a feature formed on a surface thereof configured to engage the clip to push the clip out of an end of the insertion tube or into alignment with one or more apertures in the insertion tube.

17. An injection device according to claim 13, further comprising a collar, wherein the clip is held in the partially compressed state within the collar.

18. An injection device according to claim 17, wherein the collar comprises at least one aperture, and wherein pushing the clip out of an end of the insertion tube comprises pushing the clip into alignment with the at least one aperture, thereby allowing the clip to expand.

19. An injection device according to claim 17, wherein the plunger is received within and moveable relative to the collar and the clip.

20. An injection device according to claim 17, wherein the collar comprises a rotational lock configured to prevent rotation of the clip relative to the collar.

* * * * *